(12) United States Patent
Behroozian et al.

(10) Patent No.: US 11,684,452 B2
(45) Date of Patent: Jun. 27, 2023

(54) LINGUAL SPLINT FOR HUMAN JAWS FIXATION FOR ORTHOGNATHIC SURGERY

(71) Applicants: Ahmad Behroozian, Tabriz (IR); Milad Hemmatiyan, Tabriz (IR); Sajjad Shirazi, Tabriz (IR)

(72) Inventors: Ahmad Behroozian, Tabriz (IR); Milad Hemmatiyan, Tabriz (IR); Sajjad Shirazi, Tabriz (IR)

( * ) Notice: Subject to any disclaimer, the term of this patent is extended or adjusted under 35 U.S.C. 154(b) by 1086 days.

(21) Appl. No.: 16/404,890

(22) Filed: May 7, 2019

(65) Prior Publication Data

US 2019/0254778 A1 Aug. 22, 2019

Related U.S. Application Data

(60) Provisional application No. 62/667,636, filed on May 7, 2018.

(51) Int. Cl.
*A61C 5/00* (2017.01)
*A61B 17/68* (2006.01)
*A61F 5/058* (2006.01)

(52) U.S. Cl.
CPC .............. *A61C 5/007* (2013.01); *A61B 17/68* (2013.01); *A61F 5/05891* (2013.01)

(58) Field of Classification Search
CPC ........... A61C 5/007; A61C 7/36; A61C 17/10; A61C 5/90; A61B 17/68; A61B 90/16; A61F 5/05891; A61F 5/566; Y10S 602/902; A61D 15/00
See application file for complete search history.

(56) References Cited

U.S. PATENT DOCUMENTS

2006/0174897 A1* 8/2006 Sarkisian ................ A61F 5/566
128/859
2010/0263676 A1* 10/2010 Thornton ................ A61F 5/566
128/848

\* cited by examiner

*Primary Examiner* — Cris L. Rodriguez
*Assistant Examiner* — Drew S Folgmann
(74) *Attorney, Agent, or Firm* — Bajwa IP Law Firm; Haris Zaheer Bajwa

(57) ABSTRACT

A splint for releasably fixing a maxillary jaw and a mandibular jaw of a patient together during orthognathic surgery. The splint may include a locking mechanism including a lower section and an upper section. The lower section may be attached fixedly to the mandibular jaw. The lower section may include a horizontal locking pin moveable along a horizontal axis. The upper section may include a vertical locking key attached fixedly to the maxillary jaw. The vertical locking key may include a horizontal pin receiving hole provided along a diameter of the vertical locking key. The horizontal pin receiving hole may be configured to receive the horizontal locking pin. The maxillary jaw and the mandibular jaw may be fixed together responsive to the horizontal pin receiving hole is aligned with the horizontal axis and the horizontal locking pin is inserted into the horizontal pin receiving hole.

16 Claims, 10 Drawing Sheets

LINGUAL SPLINT FOR HUMAN JAWS FIXATION FOR ORTHOGNATHIC SURGERY

CROSS-REFERENCE TO RELATED APPLICATION

This application claims the benefit of priority from U.S. Provisional Patent Application Ser. No. 62/667,636 filed on May 7, 2018, and entitled "A LINGUAL SPLINT FOR ORTHOGNATHIC SURGERY" which is incorporated herein by reference in its entirety.

TECHNICAL FIELD

The present disclosure generally relates to maxillofacial surgery systems, and particularly to a lingual splint for fixing together a maxillary jaw and a mandibular jaw of a patient for an orthognathic surgery.

BACKGROUND

The fixation of a maxillary jaw and a mandibular jaw closed together, also known as the upper and lower dental occlusal arches during orthognathic surgery is known as intermaxillary fixation or stabilization. The orthognathic surgery is employed in the treatment of some of dentofacial deformities such as mandibular or maxillary excess or deficiency, in combination with orthodontic therapy to correct and remove the deformity.

Interocclusal acrylic splint techniques represent the earliest methods of securing the maxillary jaw and mandibular jaw. The method involves utilizing heavy metallic wires that are placed in the brackets of the teeth and a custom made acrylic interocclusal splint is placed between the teeth of the jaws, and subsequently the maxillary and mandibular jaws secured to one another with a relatively light ligature wire, thus accomplishing intermaxillary fixation or stabilization and the acrylic splint maintain the correct predetermined position of the teeth. Also these surgical templates are usually unstable and bulky which may affect position of the lips and cause interferences or contact with inter-maxillary fixation and also do not provide a surgeon a clear view of interocclusal relations during the operation. Thus, surgeons are reluctant to use them. In addition, the placement, repositioning, and removal of the templates may further complicate the surgical procedure and increase the operation time. In addition, the arch wire, brackets and ball hooks, sometimes, loosen during usage and disturb the fixation competency. Also the sharp ends of the intermaxillary wire may cause irritation of the soft tissues in a patient's mouth. In addition, several steps are required, and any quicker release is not possible. There is, therefore, a need for a fixation system in an intermaxillary fixation or stabilization procedure that eliminates the inter-maxillary fixation wire and interocclusal acrylic and provides easy, quick, and accurate release and fixation of the jaws.

SUMMARY

This summary is intended to provide an overview of the subject matter of the present disclosure, and is not intended to identify essential elements or key elements of the subject matter, nor is it intended to be used to determine the scope of the claimed implementations. The proper scope of the present disclosure may be ascertained from the claims set forth below in view of the detailed description below and the drawings.

According to an exemplary embodiment, the present disclosure describes a splint for releasably fixing together a maxillary jaw and a mandibular jaw of a patient.

In an exemplary embodiment, the splint may include a lower section. In an exemplary embodiment, the lower section may be configured to be attached fixedly to the mandibular jaw. In an exemplary embodiment, the lower section may include a horizontal locking pin moveable along a horizontal axis.

In an exemplary embodiment, the locking mechanism may further include an upper section. In an exemplary embodiment, the upper section may include a vertical locking key. In an exemplary embodiment, the vertical locking key may be configured to be attached fixedly to the mandibular jaw. In an exemplary embodiment, the vertical locking key may include a horizontal pin receiving hole provided along a diameter of the vertical locking key.

In an exemplary embodiment, the horizontal pin receiving hole may be configured to receive the horizontal locking pin. In an exemplary embodiment, the maxillary jaw and the mandibular jaw may fix together responsive to the horizontal pin receiving hole receiving the horizontal locking pin.

In an exemplary embodiment, the lower section may further include a vertical hollow-cylindrical keyway. In an exemplary embodiment, the vertical hollow-cylindrical keyway may be configured to be attached fixedly to the mandibular jaw. In an exemplary embodiment, the vertical hollow-cylindrical keyway may include a vertical key receiving hole provided along a longitudinal length of the vertical hollow-cylindrical keyway. In an exemplary embodiment, the vertical key receiving hole may be configured to receive the vertical locking key.

In an exemplary embodiment, the vertical hollow-cylindrical keyway may further include a thorough horizontal pin receiving hole provided along a diameter of the vertical hollow-cylindrical keyway. In an exemplary embodiment, the horizontal locking pin may be disposed slidably inside the thorough horizontal pin receiving hole.

In an exemplary embodiment, the locking mechanism may further include a locking axis fixed relative to the mandibular jaw. In an exemplary embodiment, the horizontal axis may be aligned with the locking axis.

In an exemplary embodiment, the locking mechanism may further include a push spring supporting the horizontal locking pin. In an exemplary embodiment, the push spring may be configured to urge the horizontal locking pin to move along the locking axis responsive to the push spring being compressed.

In an exemplary embodiment, the locking mechanism may be in a locked position. In an exemplary embodiment, in the locked position, the vertical locking key may be inserted into the vertical key receiving hole. In an exemplary embodiment, in the locked position, the horizontal pin receiving hole may be aligned with the locking axis. In an exemplary embodiment, in the locked position, the horizontal locking pin may be inserted into the firs horizontal receiving hole.

In an exemplary embodiment, the locking mechanism may further be in an unlocked position. In an exemplary embodiment, in the unlocked position, the horizontal pin receiving hole may be misaligned with the locking axis.

In an exemplary embodiment, the vertical locking key may further include an inclined surface at a bottom of the vertical locking key. In an exemplary embodiment, responsive to the vertical locking key moving down inside the vertical key receiving hole, the inclined surface may urge the horizontal locking pin to move back against the push spring and compress the push spring. In an exemplary embodiment, the horizontal pin receiving hole may be positioned immediately above the inclined surface.

In an exemplary embodiment, responsive to the inclined surface is passed down over the locking axis and the horizontal pin receiving hole is aligned with the locking axis, the compressed push spring may push the horizontal locking pin into the horizontal pin receiving hole.

In an exemplary embodiment, the lower section may further include a lower attachment member. In an exemplary embodiment, the lower attachment may be configured to be attached fixedly to a lingual surface of the mandibular row of teeth. In an exemplary embodiment, the vertical hollow-cylindrical keyway may be attached fixedly to the lower attachment member.

In an exemplary embodiment, the lower attachment member may include an outer surface. In an exemplary embodiment, the outer surface may be configured to be in contact with the lingual surface of the mandibular row of teeth. In an exemplary embodiment, the lower attachment member may be attached fixedly at the outer surface of the lower attachment member to the lingual surface of the mandibular row of teeth.

In an exemplary embodiment, the upper section may include an upper attachment member. In an exemplary embodiment, the upper attachment member may be configured to be attached fixedly to a lingual surface of the maxillary row of teeth. In an exemplary embodiment, the vertical locking key may be attached fixedly to the upper attachment member.

In an exemplary embodiment, the upper attachment member may include an outer surface configured to be in contact matching with the lingual surface of the maxillary row of teeth. In an exemplary embodiment, the upper attachment member may be configured to be attached fixedly at the outer surface of the upper attachment member to the lingual surface of the maxillary row of teeth.

In an exemplary embodiment, the lower attachment member may include a top surface. In an exemplary embodiment, the top surface may include a lower zigzag-shaped profile. In an exemplary embodiment, the upper attachment may include a bottom surface. In an exemplary embodiment, the bottom surface may include an upper zigzag-shaped profile. In an exemplary embodiment, the lower zigzag-shaped profile and the upper zigzag-shaped profile may be mated to each other in the locked position of the locking mechanism.

In an exemplary embodiment, the splint may further include a release mechanism, in an exemplary embodiment, the release mechanism may be configured to allow the maxillary jaw's movements relative to the mandibular jaw by pulling out the horizontal locking pin.

In an exemplary embodiment, the release mechanism may include a ligature wire attached fixedly to the horizontal locking pin. In an exemplary embodiment, the horizontal locking pin may be pulled out from the horizontal pin receiving hole and to thereby the upper jaw's movements relative to the lower jaw may be allowed responsive to the ligature wire being pulled.

BRIEF DESCRIPTION OF THE DRAWINGS

The drawing figures depict one or more implementations in accord with the present teachings, by way of example only, not by way of limitation. In the figures, like reference numerals refer to the same or similar elements.

DETAILED DESCRIPTION

In the following detailed description, numerous specific details are set forth by way of examples in order to provide a thorough understanding of the relevant teachings. However, it should be apparent that the present teachings may be practiced without such details. In other instances, well-known methods, procedures, components, and/or circuitry have been described at a relatively high-level, without detail, in order to avoid unnecessarily obscuring aspects of the present teachings. The following detailed description is presented to enable a person skilled in the art to make and use the methods and devices disclosed in exemplary embodiments of the present disclosure. For purposes of explanation, specific nomenclature is set forth to provide a thorough understanding of the present disclosure. However, it will be apparent to one skilled in the art that these specific details are not required to practice the disclosed exemplary embodiments. Descriptions of specific exemplary embodiments are provided only as representative examples. Various modifications to the exemplary implementations will be readily apparent to one skilled in the art, and the general principles defined herein may be applied to other implementations and applications without departing from the scope of the present disclosure. The present disclosure is not intended to be limited to the implementations shown but is to be accorded the widest possible scope consistent with the principles and features disclosed herein.

Herein is disclosed an exemplary splint for releasably fixing together a maxillary jaw and a mandibular jaw of a patient during orthognathic surgery. The exemplary splint provides a facility for a dentist and/or a surgeon to fix together the maxillary jaw and the mandibular jaw of a patient easily and quickly when the surgeon intends to implement a surgical operation on the patient that necessitates the patient's jaws fixation.

Furthermore, the exemplary splint may provide a facility for a dentist and/or a surgeon to release a patient's jaws fixation simply and quickly. An exemplary splint may include an upper locking member that may be attached to a maxillary row of teeth and a lower locking member that may be attached to a mandibular row of teeth. When a patient closes his/her jaws, an upper locking member and a lower locking member may be latched together. An exemplary splint may further include a release ligature wire. A dentist and/or surgeon may be able to release a patient's jaws fixation by simply and quickly pulling a release ligature wire.

Figure 1:
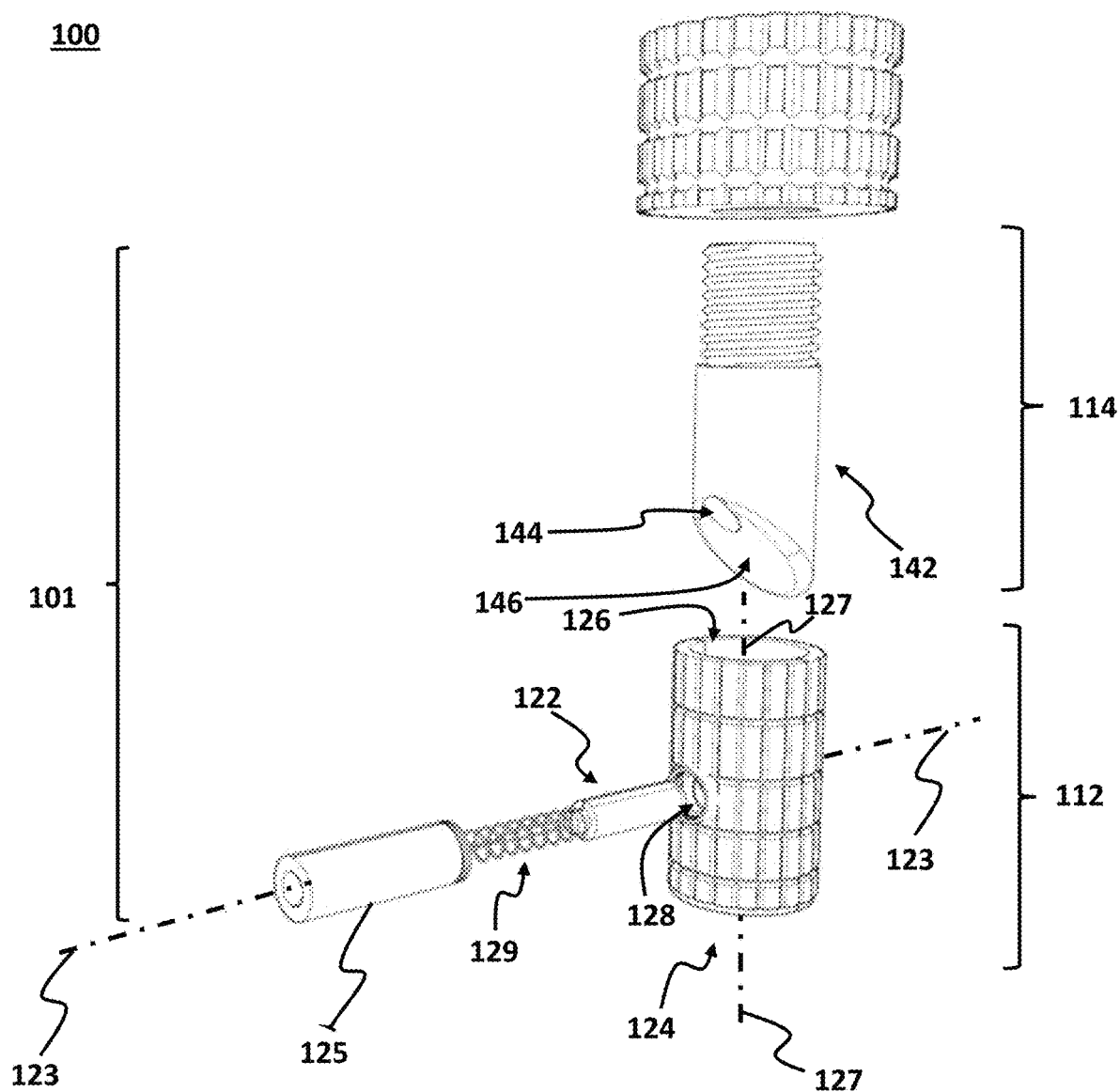
FIG. 1 illustrates an exemplary locking mechanism for releasably fixing a maxillary jaw and a mandibular jaw of a patient together, consistent with one or more exemplary embodiments of the present disclosure.
Figure 2:
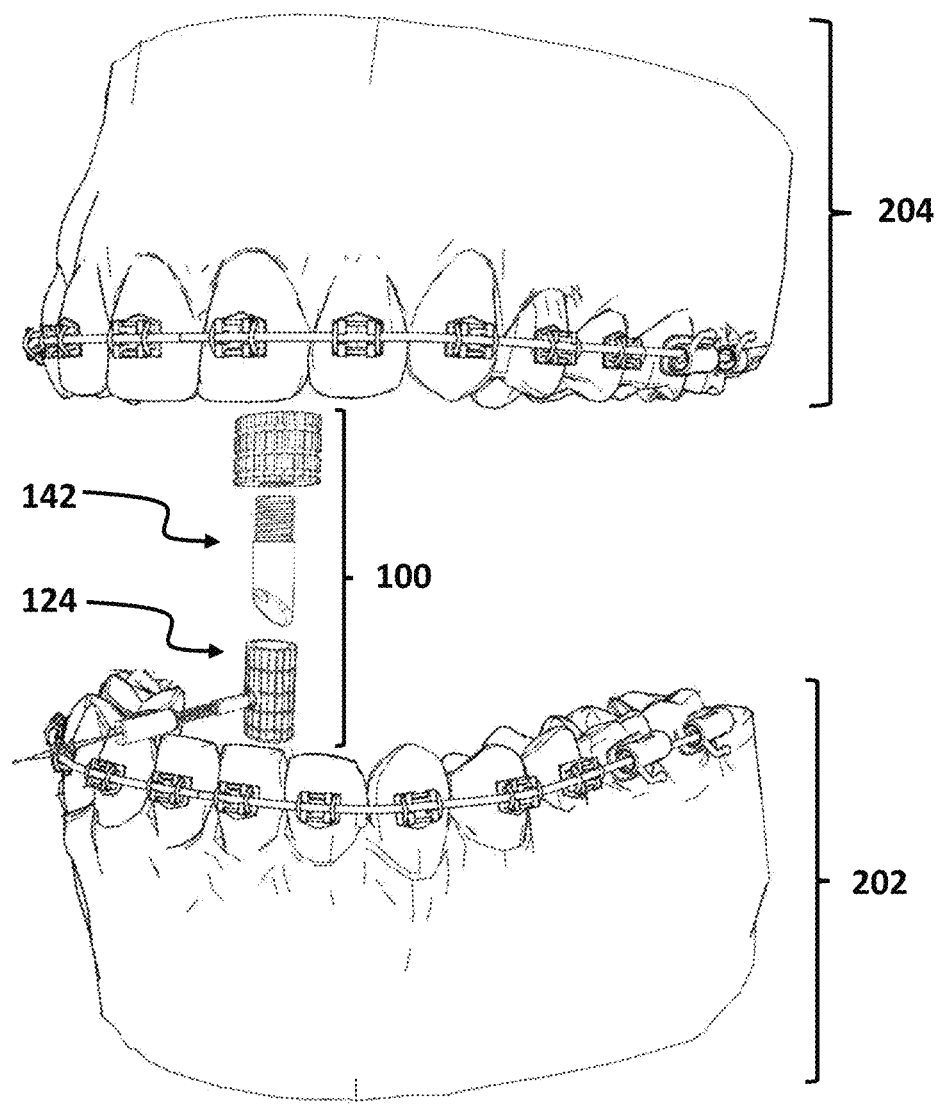
FIG. 2 illustrates an exemplary splint, a mandibular jaw, and a maxillary jaw of a patient, consistent with one or more exemplary embodiments of the present disclosure.

FIG. 1 shows an exemplary locking mechanism for releasably fixing together a maxillary jaw and a mandibular jaw of a patient, consistent with one or more exemplary embodiments of the present disclosure. FIG. 2 shows an exemplary splint, a mandibular jaw, and a maxillary jaw of a patient, consistent with one or more exemplary embodiments of the present disclosure. As shown in FIG. 1 and FIG. 2, in an exemplary embodiment, splint 100 may include a locking mechanism 101. In an exemplary embodiment, locking mechanism 101 may include a lower section 112 attached fixedly to mandibular jaw 202 of a patient. In an exemplary embodiment, mandibular jaw 202 of a patient may refer to an upper jaw of a patient. In an exemplary embodiment, lower section 112 may include a horizontal locking pin 122 moveable along a horizontal axis 123. In an exemplary embodiment, lower section 112 may further include a hollow cylindrical keyway 124. In an exemplary embodiment, hollow cylindrical keyway 124 may be implanted in mandibular jaw 202 of a patient. In an exemplary embodiment, hollow cylindrical keyway 124 may have a hollow cylindrical shape.

In an exemplary embodiment, an internal diameter of hollow cylindrical keyway 124 may correspond to an external diameter of horizontal locking pin 122. In an exemplary embodiment, hollow cylindrical keyway 124 may be placed in a line with horizontal axis 123, and horizontal locking pin 123 may be disposed slidably inside hollow cylindrical keyway 124, and consequently, horizontal locking pin 123 may be limited to move along horizontal axis 123. In an exemplary embodiment, it may be understood that splint 100 is scaled up in FIG. 2 to provide clarity with regards to functionality. In an exemplary embodiment, a size of splint 100 may be smaller than the size of splint 100 relative to mandibular jaw 202 and maxillary jaw 204 as illustrated in FIG. 2.

In an exemplary embodiment, locking mechanism 100 may further include an upper section 114 including a vertical locking key 142 moveable along a vertical axis 127. In an exemplary embodiment, vertical locking key 142 may be attached fixedly to maxillary jaw 204 of a patient. In an exemplary embodiment, maxillary jaw 204 of a patient may refer to a lower jaw of a patient. In an exemplary embodiment, vertical locking key 142 may include a horizontal pin receiving hole 144 provided along a diameter of vertical locking key 142. In an exemplary embodiment, vertical locking key 142 may include a substantially cylindrical shape. In an exemplary embodiment, horizontal pin receiving hole 144 may be configured to receive horizontal locking pin 122. In an exemplary embodiment, an inner diameter of horizontal pin receiving hole 144 may correspond to the external diameter of horizontal locking pin 122. In an exemplary embodiment, the correspondence between the inner diameter of horizontal pin receiving hole 144 and the external diameter of horizontal locking pin 122 may refer to corresponding sizes so that horizontal locking pin 122 may be able to fit within horizontal pin receiving hole 144. In an exemplary embodiment, maxillary jaw 204 and mandibular jaw 202 may be fixed together responsive to horizontal pin receiving hole 144 being aligned with horizontal axis 123 and horizontal locking pin 122 being inserted into horizontal pin receiving hole 144. In an exemplary embodiment, it may be understood that when a patient closes his/her jaws, vertical locking key 142 may move down along vertical axis 127 and when a patient's jaws are closed, horizontal pin receiving hole 144 may be aligned with horizontal axis 123. Then, when horizontal locking pin 122 is inserted into horizontal pin receiving hole 144, maxillary jaw 204 and mandibular jaw 202 of the patient may be locked or, otherwise, fixed together.

In an exemplary embodiment, lower section 122 may further include a vertical hollow-cylindrical keyway 124. In an exemplary embodiment, vertical hollow-cylindrical keyway 124 may be attached fixedly to mandibular jaw 202. In an exemplary embodiment, vertical hollow-cylindrical keyway 124 may include a vertical key receiving hole 126. In an exemplary embodiment, vertical key receiving hole 126 may be provided along vertical axis 127. In an exemplary embodiment, vertical key receiving hole 126 may be configured to receive vertical locking key 142. In an exemplary embodiment, vertical hollow-cylindrical keyway 124 may further include a thorough horizontal pin receiving hole 128. In an exemplary embodiment, the term "thorough hole" may refer to a hole that is open at both ends thereof. In an exemplary embodiment, thorough horizontal pin receiving hole 128 may be provided along horizontal axis 123. In an exemplary embodiment, horizontal locking pin 122 may be disposed slidably inside thorough horizontal pin receiving hole 128.

Figure 3:
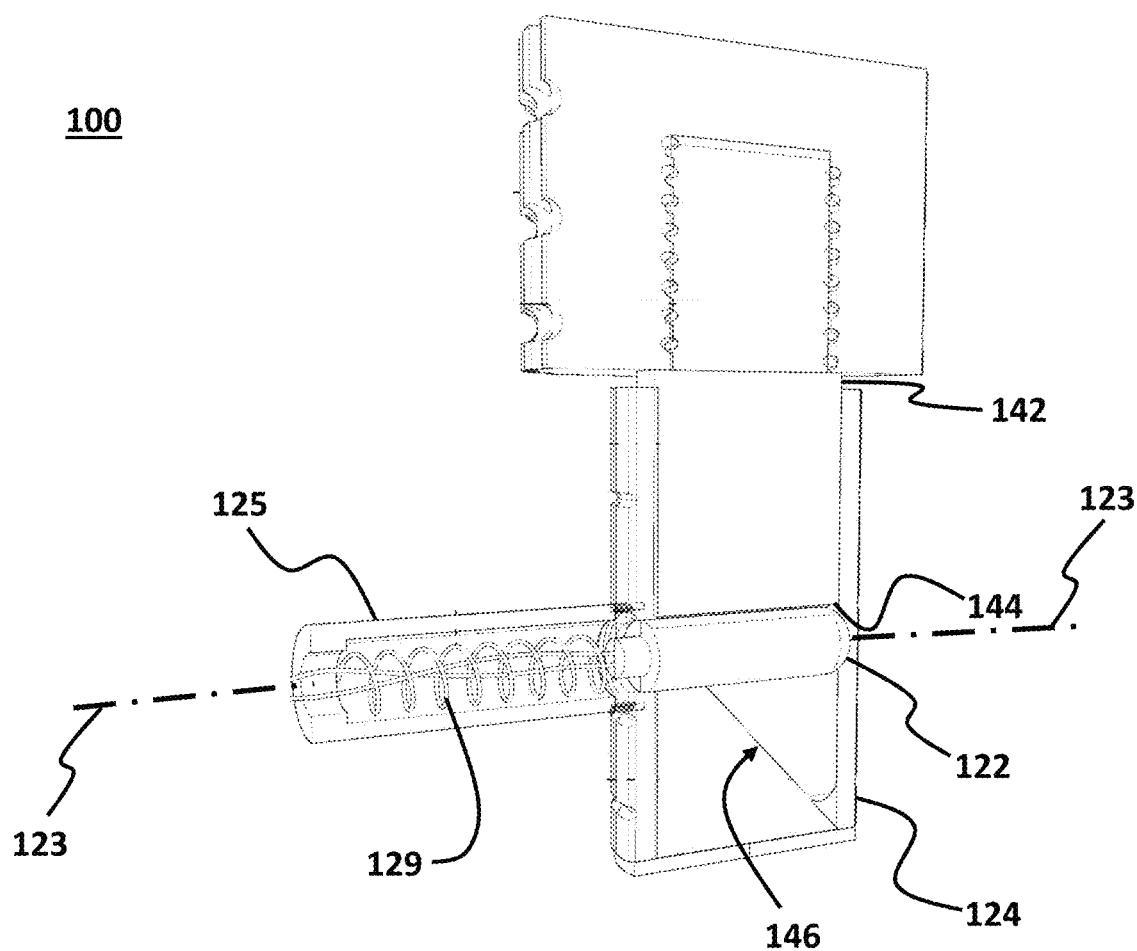
FIG. 3 illustrates a sectional view of an exemplary splint when the locking mechanism is in a locked position, consistent with one or more exemplary embodiments of the present disclosure.
Figure 4:
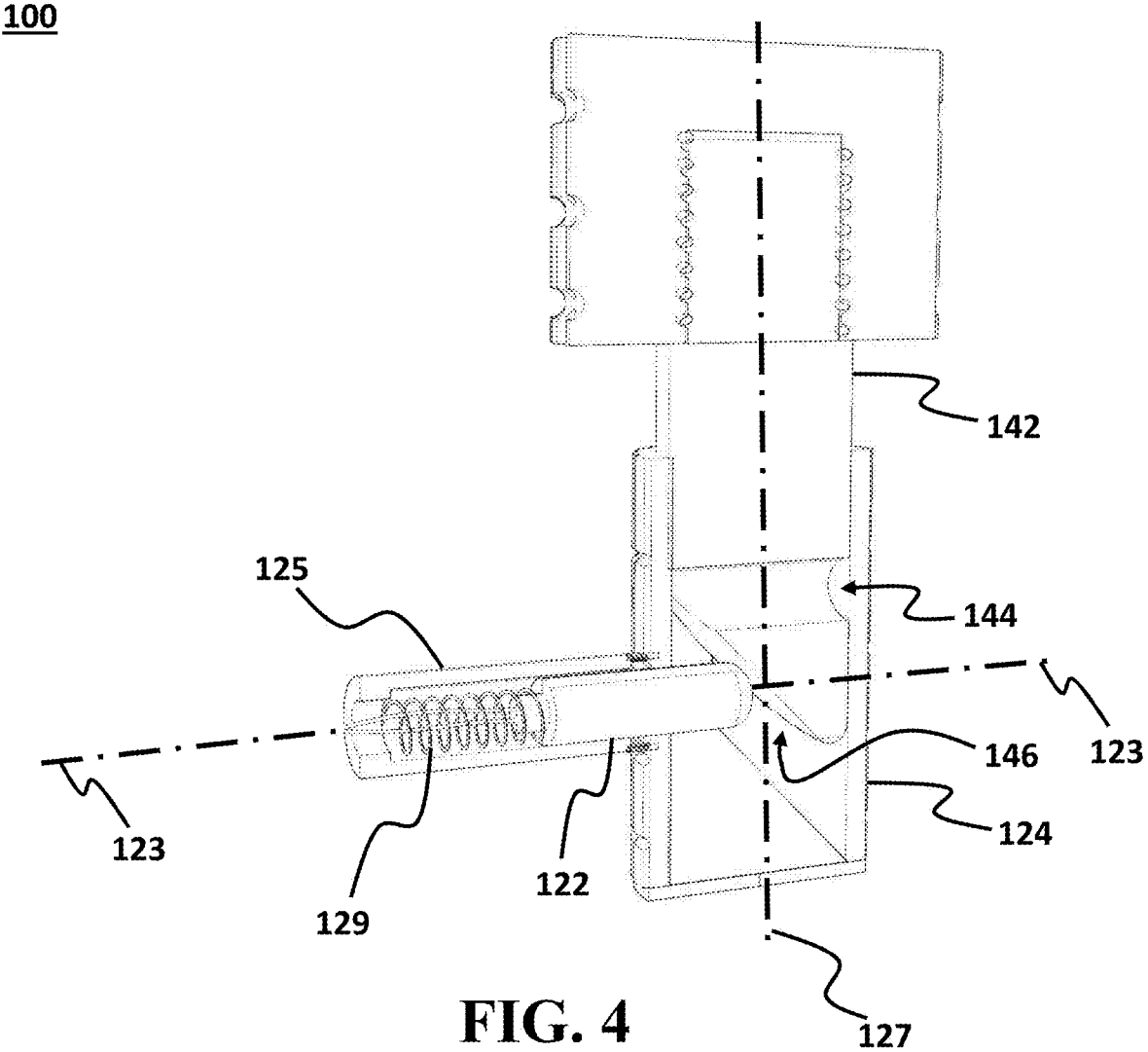
FIG. 4 illustrates a sectional view of an exemplary splint when the locking mechanism is in an unlocked position, consistent with one or more exemplary embodiments of the present disclosure.

As shown in FIG. 1, FIG. 3, and FIG. 4, in an exemplary embodiment, locking mechanism may further include a push spring 129 supporting horizontal locking pin 122. In an exemplary embodiment, push spring 129 may be disposed adjacent to horizontal locking pin 122. In an exemplary embodiment, when push spring 129 is released, push spring 129 may urge horizontal locking pin 122 to move along horizontal axis 123. In an exemplary embodiment, push spring 129 may be configured to push horizontal locking pin 122 into horizontal pin receiving hole 144 when horizontal pin receiving hole 144 is aligned with horizontal axis 123.

FIG. 3 shows a sectional view of an exemplary splint when the locking mechanism is in a locked position, consistent with one or more exemplary embodiments of the present disclosure. In an exemplary embodiment, locking mechanism 101 may be in a locked position. In an exemplary embodiment, locked position may refer to a configuration of locking mechanism 101 at which the patient's jaws fixation is realized in the predetermined occlusion and, consequently, a patient may not be able to open his/her jaws. In an exemplary embodiment, occlusion may refer to a relationship between maxillary and mandibular teeth when they approach each other.

In an exemplary embodiment, as shown in FIG. 3, in the locked position, vertical locking key 142 may be inserted into vertical key receiving hole 126. In an exemplary embodiment, it may be understood that when a surgeon closes the patient's jaws, locking key 142 may be inserted into vertical key receiving hole 126. Furthermore, in an exemplary embodiment, in the locked position, horizontal pin receiving hole 144 may be aligned with horizontal axis 123. In an exemplary embodiment, horizontal pin receiving hole 144 may be provided at a predetermined height of vertical locking key 142 such that when the patient closes his/her jaws together, horizontal pin receiving hole 144 is aligned with horizontal axis 123. In an exemplary embodiment, in the locked position, horizontal locking pin 144 may be inserted into horizontal pin receiving hole 144 by the pressure of push spring 129 and to thereby maxillary jaw's 204 movements relative to the mandibular jaw 202 may be prevented or otherwise minimized. In an exemplary embodiment, in the locked position, when horizontal pin receiving hole 144 is aligned with horizontal axis 123, push spring 129 may push horizontal locking pin 122 into horizontal pin receiving hole 144.

FIG. 4 shows a sectional view of an exemplary splint when the locking mechanism is in an unlocked position, consistent with one or more exemplary embodiments of the present disclosure. As shown in FIG. 4, in an exemplary embodiment, locking mechanism 101 may further be in an unlocked position. In an exemplary embodiment, unlocked position may refer to a configuration of locking mechanism 101 at which mandibular jaw 202 and maxillary jaw 204 are not fixed together and, consequently, the patient is able to open his/her jaws. In an exemplary embodiment, in the unlocked position, horizontal pin receiving hole 144 may be misaligned with horizontal axis 123. In an exemplary embodiment, the unlocked position of locking mechanism 101 may be realized when horizontal locking pin 122 is not present within horizontal pin receiving hole 144 and, consequently, vertical locking key 142 may be allowed to move up and down along vertical axis 127.

As shown in FIG. 1, FIG. 3, and FIG. 4, in an exemplary embodiment, vertical locking key 142 may further include an inclined surface 146. In an exemplary embodiment, inclined surface 146 may be provided at a bottom of vertical locking key 142. In an exemplary embodiment, as shown in FIG. 4, when vertical locking key 142 moves down along vertical axis 127 and inside vertical key receiving hole 126, inclined surface 146 may urge horizontal locking pin 122 to move back along horizontal axis 123 and against push spring 129 and, consequently, horizontal locking pin 122 may compress push spring 129. In an exemplary embodiment, horizontal pin receiving hole 144 may be placed at a top portion of inclined surface 146. In an exemplary embodiment, push spring 129 may be configured to help maintain contact between horizontal locking pin 122 and inclined surface 146.

In an exemplary embodiment, when vertical locking key 142 moves down along vertical axis 127 and inside vertical key receiving hole 126, and horizontal pin receiving hole 144 is aligned with horizontal axis 123, compressed push spring 129 may push horizontal locking pin 122 into horizontal pin receiving hole 144.

Figure 5:
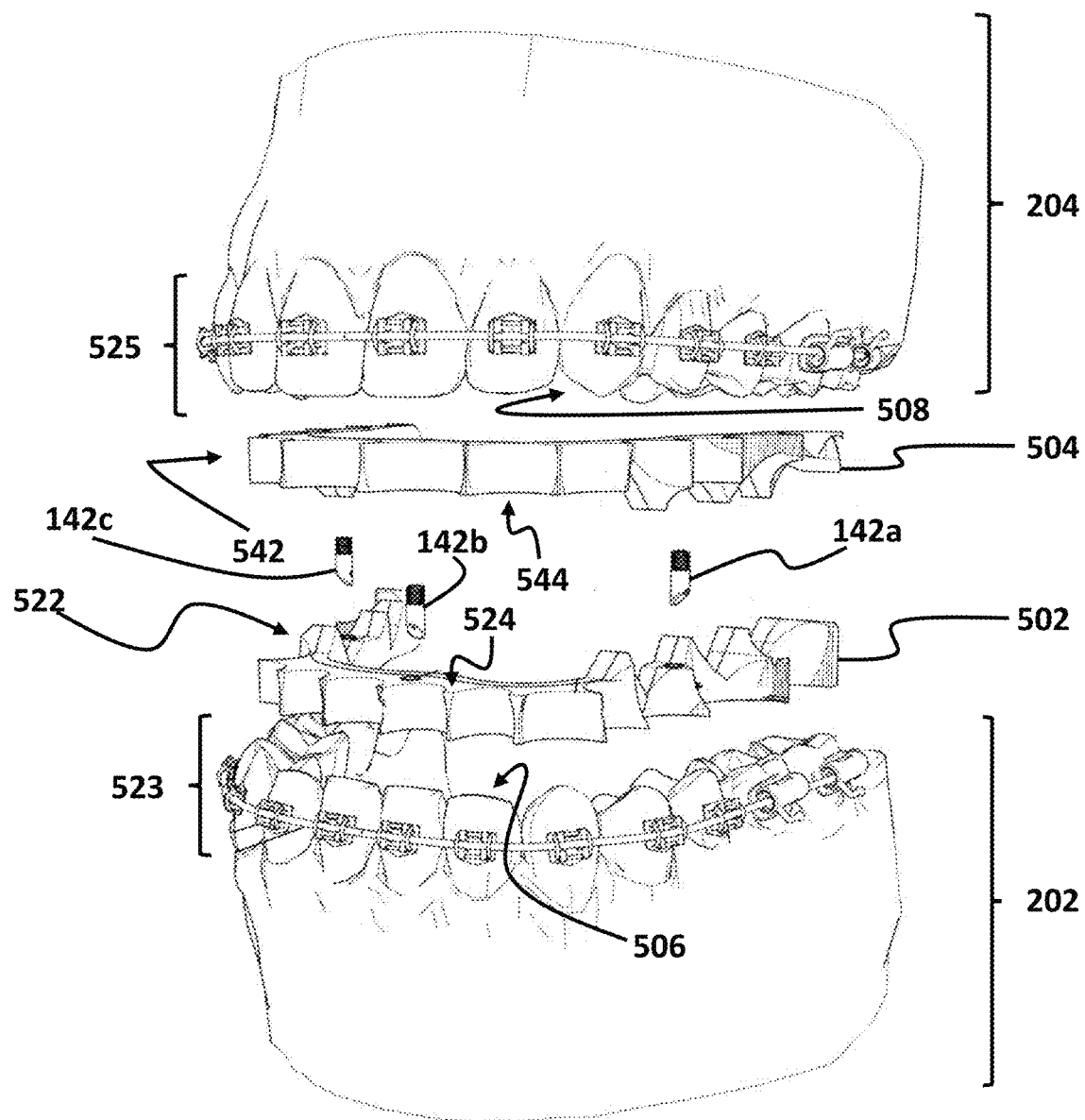
FIG. 5 illustrates a maxillary jaw, a mandibular jaw, and a pair of exemplary attachment members, consistent with one or more exemplary embodiments of the present disclosure.

FIG. 5 shows a maxillary jaw, a mandibular jaw, and a pair of exemplary attachment members, consistent with one or more exemplary embodiments of the present disclosure. As shown in FIG. 5, in an exemplary embodiment, lower section 112 may further include a lower attachment member 502. In an exemplary embodiment, lower attachment member 502 may be attached fixedly to a lower lingual surface 506 of mandibular row of teeth 523. In an exemplary embodiment, lower lingual surface 506 of mandibular row of teeth 523 may refer to a surface of mandibular row of teeth 523 which faces towards a patient's tongue. In an exemplary embodiment, vertical hollow-cylindrical keyway 124 may be attached fixedly to lower attachment member 502. In an exemplary embodiment, lower attachment member 502 may include a lower outer surface 522 configured to be in contact with lower lingual surface 506 of mandibular row of teeth 523. In an exemplary embodiment, lower attachment member 502 may be attached fixedly at lower outer surface 522 of lower attachment member 502 to lower lingual surface 506 of mandibular row of teeth 523. In an exemplary embodiment, for a specific patient, lower outer surface 522 of lower attachment member 502 may be shaped based on shape of the lower lingual surface of mandibular row of teeth of the specific patient.

In an exemplary embodiment, upper section 114 may include an upper attachment member 504. In an exemplary embodiment, upper attachment member 504 may be attached fixedly to an upper lingual surface 508 of maxillary row of teeth 525. In an exemplary embodiment, upper lingual surface 508 of maxillary row of teeth 525 may refer to a surface of maxillary row of teeth 525 which faces towards a patient's tongue. In an exemplary embodiment, vertical locking key 142 may be attached fixedly to upper attachment member 504. In an exemplary embodiment, upper attachment member 504 may include an upper outer surface 542 configured to be in contact with upper lingual surface 508 of maxillary row of teeth 525. In an exemplary embodiment, upper attachment member 504 may be attached fixedly at upper outer surface 542 of upper attachment member 504 to upper lingual surface 508 of maxillary row of teeth 525. In an exemplary embodiment, for a specific patient, upper outer surface 542 of upper attachment member 504 may be shaped based on shape of the upper lingual surface of maxillary row of teeth of the patient. For purpose of reference, it should be understood that each of pins 142$a$, 142$b$, and 142$c$ shown in FIG. 5 may be substantially analogous to vertical locking key 142 shown in FIG. 1.

Figure 6:
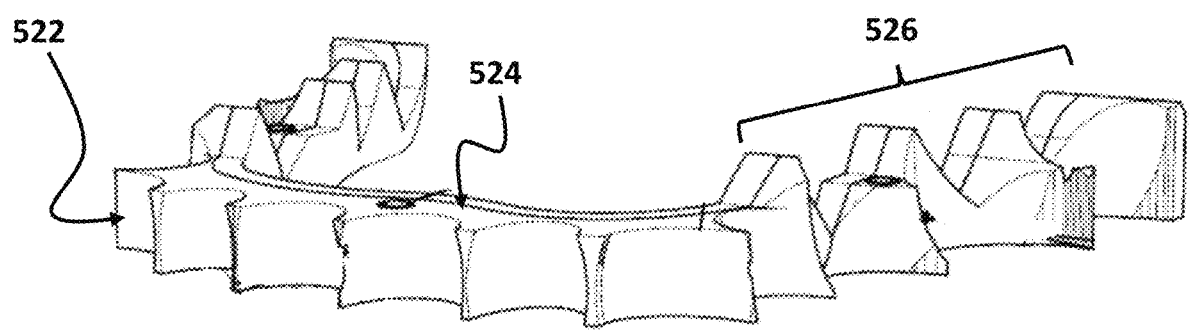
FIG. 6 illustrates an exemplary lower attachment member, consistent with one or more exemplary embodiments of the present disclosure.
Figure 6:
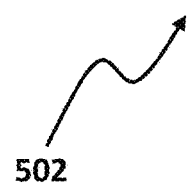

FIG. 6 shows an exemplary lower attachment member, consistent with one or more exemplary embodiments of the present disclosure. As shown in FIG. 6, in an exemplary embodiment, lower attachment member 502 may include a top surface 524. In an exemplary embodiment, top surface 524 may include a lower zigzag-shaped profile 526. In an exemplary embodiment, the term "profile" may refer to a shape of top surface 524 of lower attachment member 502.

Figure 7:
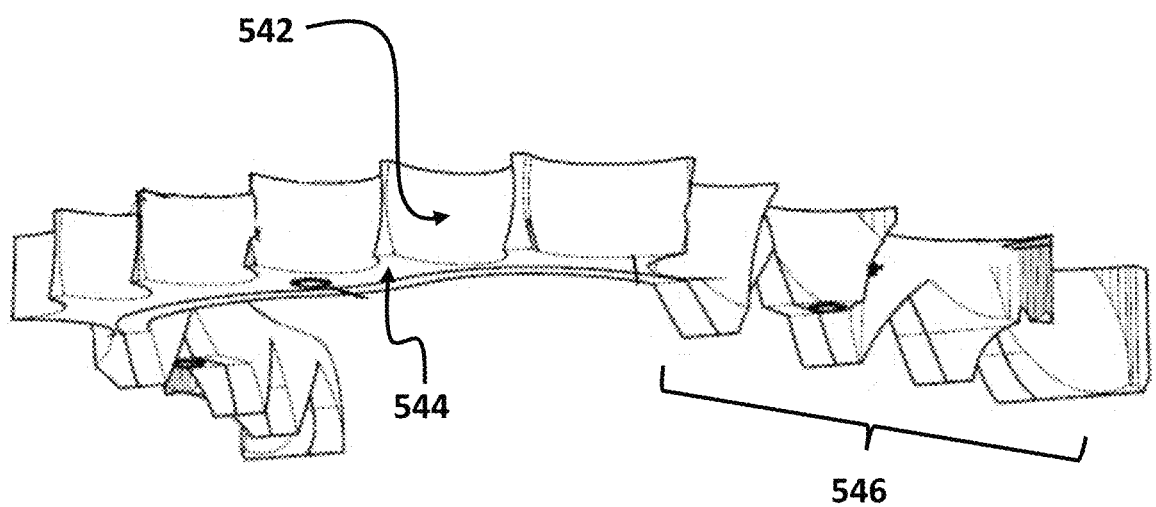
FIG. 7 illustrates an exemplary upper attachment member, consistent with one or more exemplary embodiments of the present disclosure.
Figure 7:
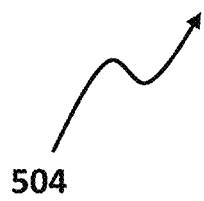

FIG. 7 shows an exemplary upper attachment member, consistent with one or more exemplary embodiments of the present disclosure. As shown in FIG. 7, in an exemplary embodiment, upper attachment member 504 may include a bottom surface 544. In an exemplary embodiment, bottom surface 544 may include an upper zigzag-shaped profile 546. In an exemplary embodiment, the term "profile" may refer to a shape of bottom surface 544 of lower attachment member 504.

Figure 8:
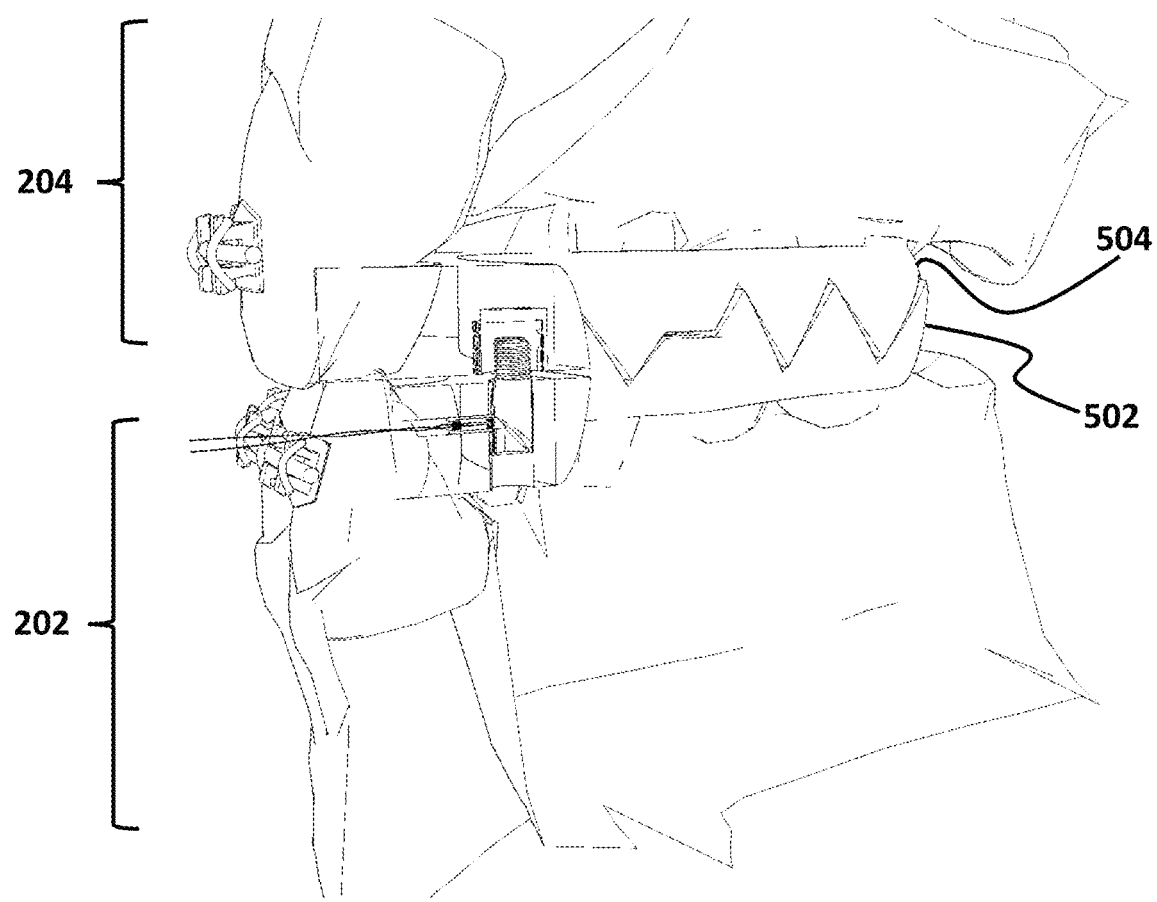
FIG. 8 illustrates an exemplary lower attachment member and an exemplary upper attachment member mated to each other when a patient's jaws are closed, consistent with one or more exemplary embodiments of the present disclosure.
Figure 9:
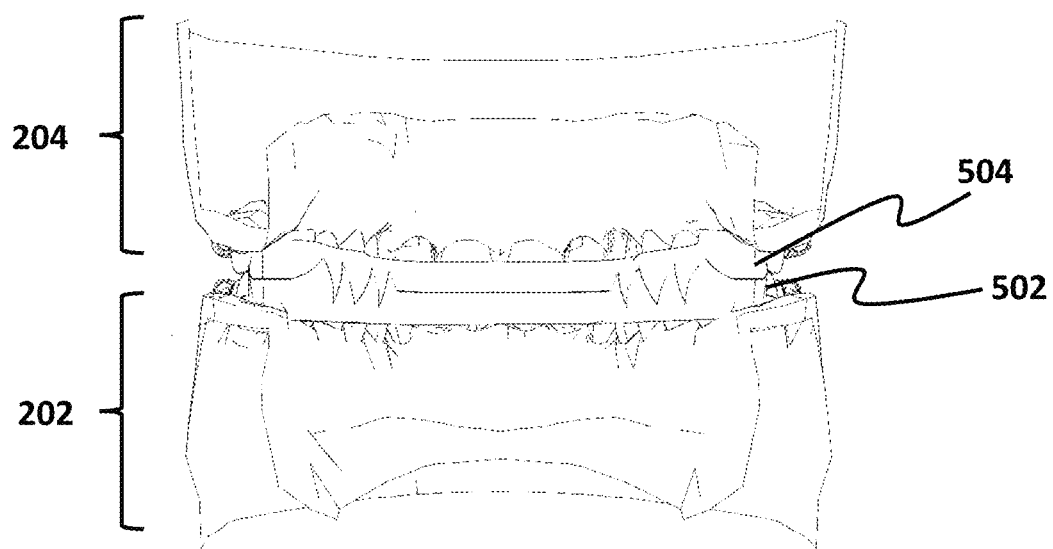
FIG. 9 illustrates a back view of an exemplary lower attachment member and an exemplary upper attachment member mated to each other when a patient's jaws are closed, consistent with one or more exemplary embodiments of the present disclosure.

FIG. 8 shows an exemplary lower attachment member and an exemplary upper attachment member mated to each other when a patient's jaws are closed, consistent with one or more exemplary embodiments of the present disclosure. FIG. 9 shows a back view of an exemplary lower attachment member and an exemplary upper attachment member mated to each other when a patient's jaws are closed, consistent with one or more exemplary embodiments of the present disclosure. As shown in FIG. 8 and FIG. 9, in an exemplary embodiment, lower zigzag-shaped profile 526 and upper zigzag-shaped profile 546 may be configured to help maintain contact between top surface 524 of lower attachment member 502 and bottom surface 544 of upper attachment member 504. In an exemplary embodiment, benefits from utilizing lower zigzag-shaped profile 526 and upper zigzag-shaped profile 546 may include, but are not limited to, a facility improving simplicity and accuracy of a patient's jaws fixation. Furthermore, utilizing lower zigzag-shaped profile 526 and upper zigzag-shaped profile 546 may provide highly reliable positioning of maxillary jaw 204 and mandibular jaw 202 to each other. Also, it may help a patient to close his/her jaws simply and correctly in a predetermined position in postsurgical phase.

Figure 10:
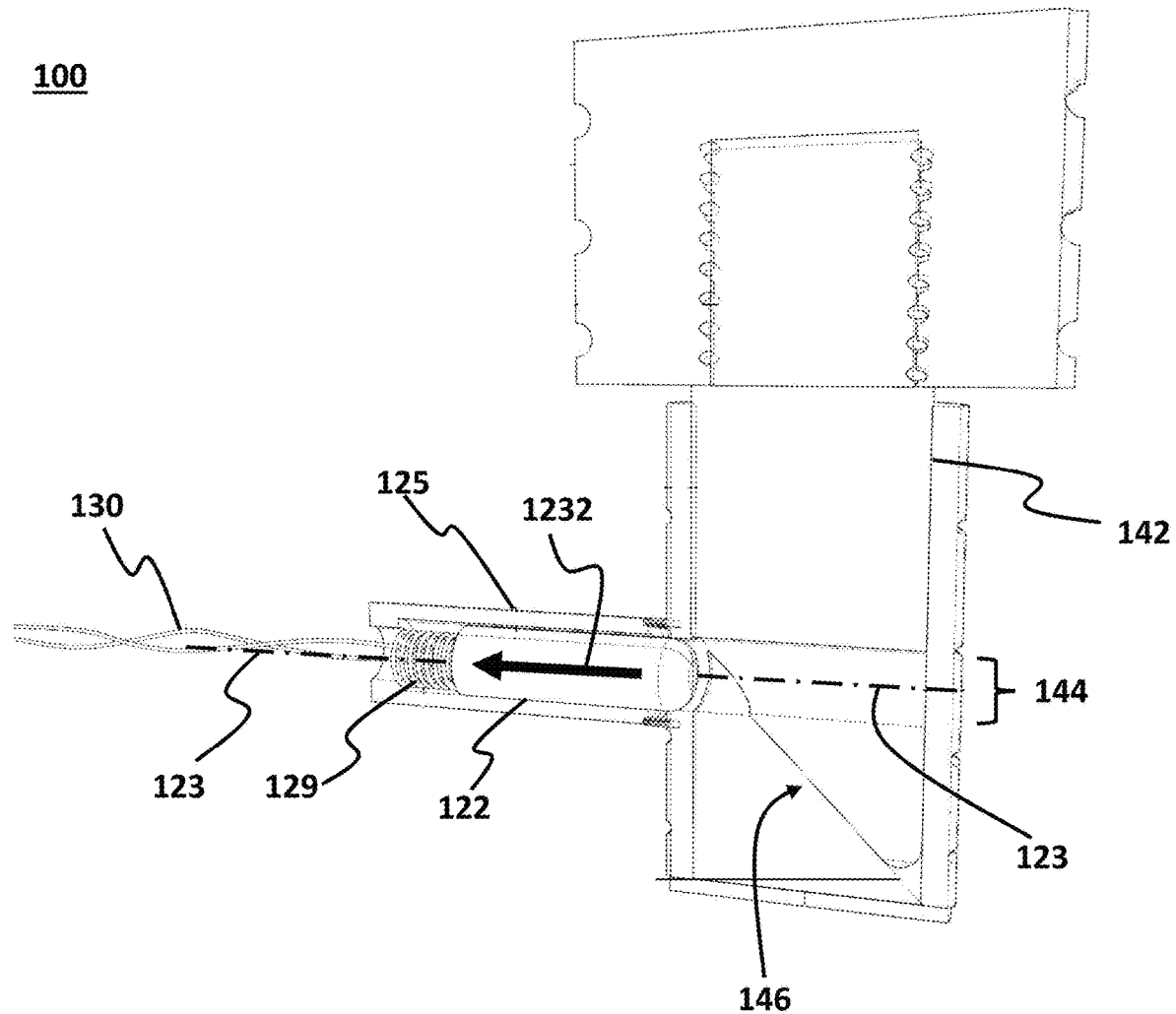
FIG. 10 illustrates an exemplary splint with a release mechanism, consistent with one or more exemplary embodiments of the present disclosure.

FIG. 10 shows an exemplary splint with a release mechanism, consistent with one or more exemplary embodiments of the present disclosure. As shown in FIG. 10, in an exemplary embodiment, locking mechanism 101 may further include a release mechanism including a ligature wire 130 attached fixedly to horizontal locking pin 122. In an exemplary embodiment, ligature wire 130 may be configured to pull out horizontal locking pin 122 from horizontal pin receiving hole 144 and thereby allowing maxillary jaw's 204 movements relative to mandibular jaw 202. In an exemplary embodiment, it may be understood that a surgeon may be able to release the jaws fixation by pulling out horizontal locking pin 122 from horizontal pin receiving hole 144 through pulling ligature wire 130 in an exemplary direction shown by arrow 1232. In an exemplary embodiment, utilizing ligature wire 130 as a release mechanism may provide significant benefits including but not limited to a facility for release the patient's jaws fixation easily and quickly. For purpose of reference, it could be understood that, in an exemplary embodiment, ligature wire 130 may then be tied to a main orthodontic arch wire. In an exemplary embodiment, the disclosed release facility including ligature wire 130 may be able to reduce clinician's error during surgery as well as pre-surgical and post-surgical phases.

While the foregoing has described what are considered to be the best mode and/or other examples, it is understood that various modifications may be made therein and that the subject matter disclosed herein may be implemented in various forms and examples, and that the teachings may be applied in numerous applications, only some of which have been described herein. It is intended by the following claims to claim any and all applications, modifications and variations that fall within the true scope of the present teachings.

Unless otherwise stated, all measurements, values, ratings, positions, magnitudes, sizes, and other specifications that are set forth in this specification, including in the claims that follow, are approximate, not exact. They are intended to have a reasonable range that is consistent with the functions to which they relate and with what is customary in the art to which they pertain.

The scope of protection is limited solely by the claims that now follow. That scope is intended and should be interpreted to be as broad as is consistent with the ordinary meaning of the language that is used in the claims when interpreted in light of this specification and the prosecution history that follows and to encompass all structural and functional equivalents. Notwithstanding, none of the claims are intended to embrace subject matter that fails to satisfy the requirement of Sections 101, 102, or 103 of the Patent Act, nor should they be interpreted in such a way. Any unintended embracement of such subject matter is hereby disclaimed.

Except as stated immediately above, nothing that has been stated or illustrated is intended or should be interpreted to cause a dedication of any component, step, feature, object, benefit, advantage, or equivalent to the public, regardless of whether it is or is not recited in the claims.

It will be understood that the terms and expressions used herein have the ordinary meaning as is accorded to such terms and expressions with respect to their corresponding respective areas of inquiry and study, except where specific meanings have otherwise been set forth herein. Relational terms such as "first" and "second" and the like may be used solely to distinguish one entity or action from another without necessarily requiring or implying any actual such relationship or order between such entities or actions. The terms "comprises," "comprising," or any other variation thereof, as used herein and in the appended claims are intended to cover a non-exclusive inclusion, encompassing a process, method, article, or apparatus that comprises a list of elements that does not include only those elements but may include other elements not expressly listed to such process, method, article, or apparatus. An element proceeded by "a" or "an" does not, without further constraints, preclude the existence of additional identical elements in the process, method, article, or apparatus that comprises the element.

The Abstract of the Disclosure is provided to allow the reader to quickly ascertain the nature of the technical disclosure. It is not intended to be used to interpret or limit the scope or meaning of the claims. In addition, in the foregoing Detailed Description, it can be seen that various features are grouped together in various implementations. Such grouping is for purposes of streamlining this disclosure and is not to be interpreted as reflecting an intention that the claimed implementations require more features than are expressly recited in each claim. Rather, as the following claims reflect, inventive subject matter lies in less than all features of a single disclosed implementation. Thus, the following claims are hereby incorporated into this Detailed Description, with each claim standing on its own as a separately claimed subject matter.

While various implementations have been described, the description is intended to be exemplary, rather than limiting and it will be apparent to those of ordinary skill in the art that many more implementations are possible that are within the scope of the implementations. Although many possible combinations of features are shown in the accompanying figures and discussed in this detailed description, many other combinations of the disclosed features are possible. Any feature of any implementation may be used in combination with or substituted for any other feature or element in any other implementation unless specifically restricted. Therefore, it will be understood that any of the features shown and/or discussed in the present disclosure may be implemented together in any suitable combination. Accordingly, the implementations are not to be restricted except in the light of the attached claims and their equivalents. Also, various modifications and changes may be made within the scope of the attached claims.

What is claimed is:

1. A splint for releasably fixing a maxillary jaw and a mandibular jaw of a patient, the splint comprising:
    a locking mechanism, the locking mechanism comprising:
        a lower section, the lower section configured to be attached fixedly to the mandibular jaw, the lower section comprising
            a horizontal locking pin, the horizontal locking pin configured to move linearly along a horizontal axis and relative to the mandibular jaw; and
        a vertical hollow-cylindrical keyway, the vertical hollow-cylindrical keyway comprising:
            a vertical key receiving hole along the vertical axis, the vertical key receiving hole configured to receive the vertical locking key; and a thorough horizontal pin receiving hole along the horizontal axis, the horizontal locking pin disposed slidably inside the thorough horizontal pin receiving hole; and an upper section comprising a vertical locking key moveable along a vertical axis, the vertical locking key configured to be attached fixedly to the maxillary jaw, the vertical locking key comprising a horizontal pin receiving hole, the horizontal pin receiving hole configured to receive the horizontal locking pin, the horizontal pin receiving hole configured to receive the horizontal locking pin to fix the maxillary jaw and the mandibular jaw together.

2. The splint of claim 1, wherein the locking mechanism further comprises a push spring supporting the horizontal locking pin, the push spring configured to urge the horizontal locking pin to move along the horizontal axis responsive to the push spring being compressed.

3. The splint of claim 2, wherein when the locking mechanism is in a locked position:
the vertical locking key is present within the vertical key receiving hole;
the horizontal pin receiving hole is aligned with the horizontal axis; and
the horizontal locking pin is present within the horizontal pin receiving hole and to thereby the maxillary jaw's movement relative to the mandibular jaw is prevented.

4. The splint of claim 3, wherein when the locking mechanism is in an unlocked position, the horizontal pin receiving hole is misaligned with the horizontal axis.

5. The splint of claim 4, wherein the vertical locking key further comprises an inclined surface at a bottom of the vertical locking key, the inclined surface configured to urge the horizontal locking pin to move back against the push spring and compress the push spring responsive to the vertical locking key moving down along the vertical axis and inside the vertical key receiving hole, the push spring configured to help maintain contact between the horizontal locking pin and the inclined surface.

6. The splint of claim 5, wherein the horizontal pin receiving hole is located at a top portion of the inclined surface.

7. The splint of claim 6, wherein the compressed push spring is configured to push the horizontal locking pin into the horizontal pin receiving hole responsive to the horizontal pin receiving hole being aligned with the horizontal axis.

8. The splint of claim 7, wherein the lower section further comprises a lower attachment member, the lower attachment member configured to be attached fixedly to a lingual surface of the mandibular row of teeth, the vertical hollow-cylindrical keyway configured to be attached fixedly to the lower attachment member.

9. The splint of claim 8, wherein the lower attachment member comprises an outer surface, the outer surface configured to be in full contact with the lingual surface of the mandibular row of teeth, the lower attachment member configured to be attached fixedly at the outer surface of the lower attachment member to the lingual surface of the mandibular row of teeth.

10. The splint of claim 9, wherein the upper section further comprises an upper attachment member, the upper attachment member configured to be attached fixedly to a lingual surface of the maxillary row of teeth, the vertical locking key configured to be attached fixedly to the upper attachment member.

11. The splint of claim 10, wherein the upper attachment member comprises an outer surface, the outer surface configured to be in full contact with the lingual surface of the maxillary row of teeth, the upper attachment member configured to be attached fixedly at the outer surface of the upper attachment member to the lingual surface of the maxillary row of teeth.

12. The splint of claim 11, wherein the lower attachment member comprises a top surface comprising a lower zigzag-shaped profile.

13. The splint of claim 12, wherein the upper attachment member comprises a bottom surface comprising an upper zigzag-shaped profile.

14. The splint of claim 13, wherein the lower zigzag-shaped profile and the upper zigzag-shaped profile are configured to mate the lower attachment member and the upper attachment member to each other through maintaining a full contact between the top surface of the lower attachment member and the bottom surface of the upper attachment member in the locked position of the locking mechanism.

15. The splint of claim 14, wherein the locking mechanism further comprises a release mechanism, the release mechanism configured to allow the maxillary jaw's movements relative to the mandibular jaw by pulling out the horizontal locking pin.

16. The splint of claim 15, wherein the release mechanism comprises a ligature wire attached fixedly to the horizontal locking pin, the release mechanism configured to allow the maxillary jaw's movement relative to the mandibular jaw responsive to the horizontal locking pin being pulled out from the horizontal pin receiving hole through pulling the ligature wire.

* * * * *